(12) United States Patent
Gomez Sanchez et al.

(10) Patent No.: US 11,276,493 B2
(45) Date of Patent: Mar. 15, 2022

(54) DEVICE CONFIGURATION BASED ON PREDICTING A HEALTH AFFLICTION

(71) Applicant: INTERNATIONAL BUSINESS MACHINES CORPORATION, Armonk, NY (US)

(72) Inventors: Francisco M. Gomez Sanchez, Córdoba (AR); Jeronimo Irazabal, Buenos Aires (AR); Pablo R. Najimovich, Buenos Aires (AR); Pablo J. Pedemonte, Buenos Aires (AR); Hernan P. Petersen, Buenos Aires (AR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 676 days.

(21) Appl. No.: 15/421,644

(22) Filed: Feb. 1, 2017

(65) Prior Publication Data

US 2018/0218123 A1    Aug. 2, 2018

(51) Int. Cl.
*G16H 50/20* (2018.01)
*G16H 40/67* (2018.01)
*G16H 40/63* (2018.01)

(52) U.S. Cl.
CPC ............. *G16H 50/20* (2018.01); *G16H 40/63* (2018.01); *G16H 40/67* (2018.01)

(58) Field of Classification Search
CPC .................................................... G16H 50/20
See application file for complete search history.

(56) References Cited

U.S. PATENT DOCUMENTS

| 8,527,213 B2 | 9/2013 | Kailas et al. |
| 2010/0318424 A1 | 12/2010 | LaValle |
| 2012/0185020 A1 | 7/2012 | Simon et al. |
| 2014/0377727 A1* | 12/2014 | Yom-Tov .............. G06F 16/951 434/236 |

(Continued)

FOREIGN PATENT DOCUMENTS

| WO | 2006021820 A1 | 3/2006 |
| WO | 2016037055 A1 | 3/2016 |

OTHER PUBLICATIONS

Prakash, J. Arun. "Eye Controlled Sensitive Screens to Adjust Brightness." Journal of Applied Global Research 5.12 (2012). (Year: 2012).*

(Continued)

*Primary Examiner* — Li B. Zhen
*Assistant Examiner* — Henry Nguyen
(74) *Attorney, Agent, or Firm* — Michael O'Keefe; Matthew M. Hulihan; Heslin Rothenberg Farley & Mesiti PC

(57) ABSTRACT

Device configuration based on predicting a health affliction. A process acquires measurements of conditions that a user is experiencing. The process predicts, based on the measurements, whether the user will experience a particular health affliction. Based on predicting that the user will experience the particular health affliction, the process configures devices of an environment in which the user is present to reduce effects of the devices on symptoms of the particular health affliction. The configuring includes adjusting a respective at least one state of each device of the devices.

16 Claims, 7 Drawing Sheets

(56) References Cited

U.S. PATENT DOCUMENTS

| | | | |
|---|---|---|---|
| 2015/0092972 A1* | 4/2015 | Lai | H04R 1/1083 |
| | | | 381/333 |
| 2015/0126824 A1 | 5/2015 | LaBoeuf et al. | |
| 2015/0223731 A1* | 8/2015 | Sahin | A61B 5/16 |
| | | | 600/301 |
| 2016/0228640 A1* | 8/2016 | Pindado | A61N 1/36139 |
| 2016/0234595 A1* | 8/2016 | Goran | G05B 15/02 |
| 2017/0139233 A1* | 5/2017 | McLendon | A61N 5/0618 |
| 2017/0165485 A1* | 6/2017 | Sullivan | A61N 1/36021 |

OTHER PUBLICATIONS

Dolle, Stephen, "Weather App helps Manage Barometric Pressure related Migraine Headache", [retrieved on Sep. 22, 2016]. Retrieved from the Internet:< URL: https://dollecommunicationsblog.wordpress.com/2015/03/06/weather-app-helps-manage-barometric-pressure-related-migraine-headache/>, Mar. 6, 2015, 17 pgs.

Young, Katy, "Data-driven healthcare app can predict an oncoming migraine", [retrieved on Sep. 22, 2016]. Retrieved from the Internet:< URL: https://www.aabacosmallbusiness.com/advisor/post/127800348727/upgrade.html>, 4 pgs.

Mell, Peter, et al., "The NIST Definition of Cloud Computing", NIST Special Publication 800-145, Sep. 2011, Gaithersburg, MD, 7 pgs.

World Health Organization—How Common are Headaches ?: [retrieved on Jan. 30, 2017]. Retrieved from the Internet:< URL: http://www.who.int/features/qa/25/en/ >, 2 pgs.

Mayo Clinic—Migraine Symptoms: [retrieved on Jan. 30, 2017]. Retrieved from the Internet:< URL: http://www.mayoclinic.org/diseases-conditions/migraine-headache/basics/symptoms/con-20026358 >, 9 pgs.

Hu, X.H., et al., "Burden of migraine in the United States: disability and economic costs": [retrieved on Jan. 30, 2017]. Retrieved from the Internet:< URL: http://www.ncbi.nlm.nih.gov/pubmed/10219926 >, Apr. 26, 1999, 2 pgs.

Tatsumoto, M., et al., "Light of Intrinsically Photosensitive Retinal Ganglion Cell (ipRGC) Causing Migraine Headache Exacerbation", Cephalalgia 33 (8 Suppl), 2013, 1 pg.

Kelman, L., "The triggers or precipitants of the acute migraine attack", [retrieved on Jan. 30, 2017]. Retrieved from the Internet:< URL: http://onlinelibrary.wiley.com/doi/10.1111/j.1468-2982.2007.01303.x/abstract >, Mar. 30, 2007, 2 pgs.

Robbins, Lawrence, "Precipitating Factors in Migraine: A Retrospective Review of 494 Patients", [retrieved on Jan. 30, 2017]. Retrieved from the Internet:< URL: http://onlinelibrary.wiley.com/doi/10.1111/j.1526-4610.1994.hed3404214.x/abstract >, Apr. 1994, 3 pgs.

Cull, R.E., "Barometric Pressure and Other Factors in Migraine", [retrieved on Jan. 30, 2017]. Retrieved from the Internet:< URL: http://onlinelibrary.wiley.com/doi/10.1111/j.1526-4610.1981.hed2103102.x/abstract >, May 1981, 3 pgs.

Prince, Patricia B., et al., "The Effect of Weather on Headache", [retrieved on Jan. 30, 2017]. Retrieved from the Internet:< URL: http://onlinelibrary.wiley.com/doi/10.1111/j.1526-4610.2004.446008.x/abstract >, Jun. 4, 2004, 3 pgs.

Friedman, Deborah, et al., "Migraine and the Environment", [retrieved on Jan. 30, 2017]. Retrieved from the Internet: < URL: http://www.researchgate.net/profile/Timothy_Dye/publication/26309868_Migraine_and_the_environment/links/02bfe50e85c2015d7c000000.pdf >, Jul. 2009, pp. 941-952.

Muaremi, A., "Towards Measuring Stress with Smartphones and Wearable Devices During Workday and Sleep", [retrieved on Jan. 30, 2017], Retrieved from the Internet:< URL: http://www.ncbi.nlm.nih.gov/pubmed/25530929 >, 2013, 2 pgs.

MacGregor, E.A., "Migraine and Menstruation: A Pilot Study", [retrieved on Jan. 30, 2017]. Retrieved from the Internet:< URL: http://cep.sagepub.com/content/10/6/305.short >, Dec. 1, 1990, 6 pgs.

Main, Alan, "Photophobia and Phonophobia in Migraineurs Between Attacks", [retrieved on Jan. 30, 2017], Retrieved from the Internet:< URL: http://onlinelibrary.wiley.com/doi/10.1046/j.1526-4610.1997.3708492.x/abstract >, Sep. 1997, 3 pgs.

* cited by examiner

DEVICE CONFIGURATION BASED ON PREDICTING A HEALTH AFFLICTION

BACKGROUND

Particular health afflictions can drastically affect a person's quality of life. Migraines, for instance, are a debilitating neurological disorder where the person suffers from severe and recurring headaches that last for a prolonged duration of time, perhaps several days. Statistics indicate that at least one in seven adults suffer from some kind of migraine. Although headaches are their main symptom, they are often accompanied by other effects including nausea or vomiting, photophobia (sensitivity to light), phonophobia (sensitivity to sounds), blurred vision, and confusion, among other symptoms.

Migraines affect the quality of life of those who suffer from them. They also negatively impact productivity. Migraines account for an estimated billions of dollars in economic loss due to work absenteeism.

Mobile devices, such as smartphones and tablets, and other devices can sometimes exacerbate the symptoms of a health affliction. For example, a person experiencing a migraine attack might present photophobia, a symptom that is made worse by the blue light emissions of a smartphone's display, and/or phonophobia, a symptom that is aggravated by the noises of incoming call rings, message alerts, application notifications and other sounds commonly emitted from the smartphone.

SUMMARY

Taking the above into account along with the fact that mobile devices are inextricably a part of our everyday lives, there is utility in being able to predict whether a user will experience a particular health affliction, such as a migraine attack, configure devices to reduce their effects on the symptoms of the affliction, and potentially leverage the devices to help the afflicted individual better deal with the debilitating condition, rather than being another aggravating factor.

Accordingly, shortcomings of the prior art are overcome and additional advantages are provided through the provision of a computer-implemented method. The method acquires measurements of conditions that a user is experiencing. The method predicts, based on the measurements, whether the user will experience a particular health affliction. Based on predicting that the user will experience the particular health affliction, the method configures devices of an environment in which the user is present to reduce effects of the devices on symptoms of the particular health affliction. The configuring includes adjusting a respective at least one state of each device of the devices.

Further, a computer program product including a computer readable storage medium readable by a processor and storing instructions for execution by the processor is provided for performing a method. The method acquires measurements of conditions that a user is experiencing. The method predicts, based on the measurements, whether the user will experience a particular health affliction. Based on predicting that the user will experience the particular health affliction, the method configures devices of an environment in which the user is present to reduce effects of the devices on symptoms of the particular health affliction. The configuring includes adjusting a respective at least one state of each device of the devices.

Yet further, a computer system is provided that includes a memory and a processor in communications with the memory, wherein the computer system is configured to perform a method. The method acquires measurements of conditions that a user is experiencing. The method predicts, based on the measurements, whether the user will experience a particular health affliction. Based on predicting that the user will experience the particular health affliction, the method configures devices of an environment in which the user is present to reduce effects of the devices on symptoms of the particular health affliction. The configuring includes adjusting a respective at least one state of each device of the devices.

Additional features and advantages are realized through the concepts described herein.

BRIEF DESCRIPTION OF THE DRAWINGS

Aspects described herein are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Described herein are non-intrusive methods to forecast health afflictions of an individual by monitoring a set of variables and using gathered information to automatically configure mobile and other devices in modes that aim to reduce the effects of those devices on symptoms of the health affliction, for instance to avoid exacerbating symptoms, and help the user deal with the health affliction. Various examples are provided herein that focus on a migraine as the particular health affliction, though this by way of example only, and not limitation; aspects described herein are readily applicable to other health afflictions.

Aspects utilize measurements of both external conditions external to the user (e.g. environmental conditions, such as barometric pressure) and internal conditions internal to the user (e.g. stress levels) as variables to forecast an affliction event. Additionally, aspects can provide an approach to automatically set device(s) into states/modes that helps a user better deal with the symptoms during an affliction event.

Figure 1:
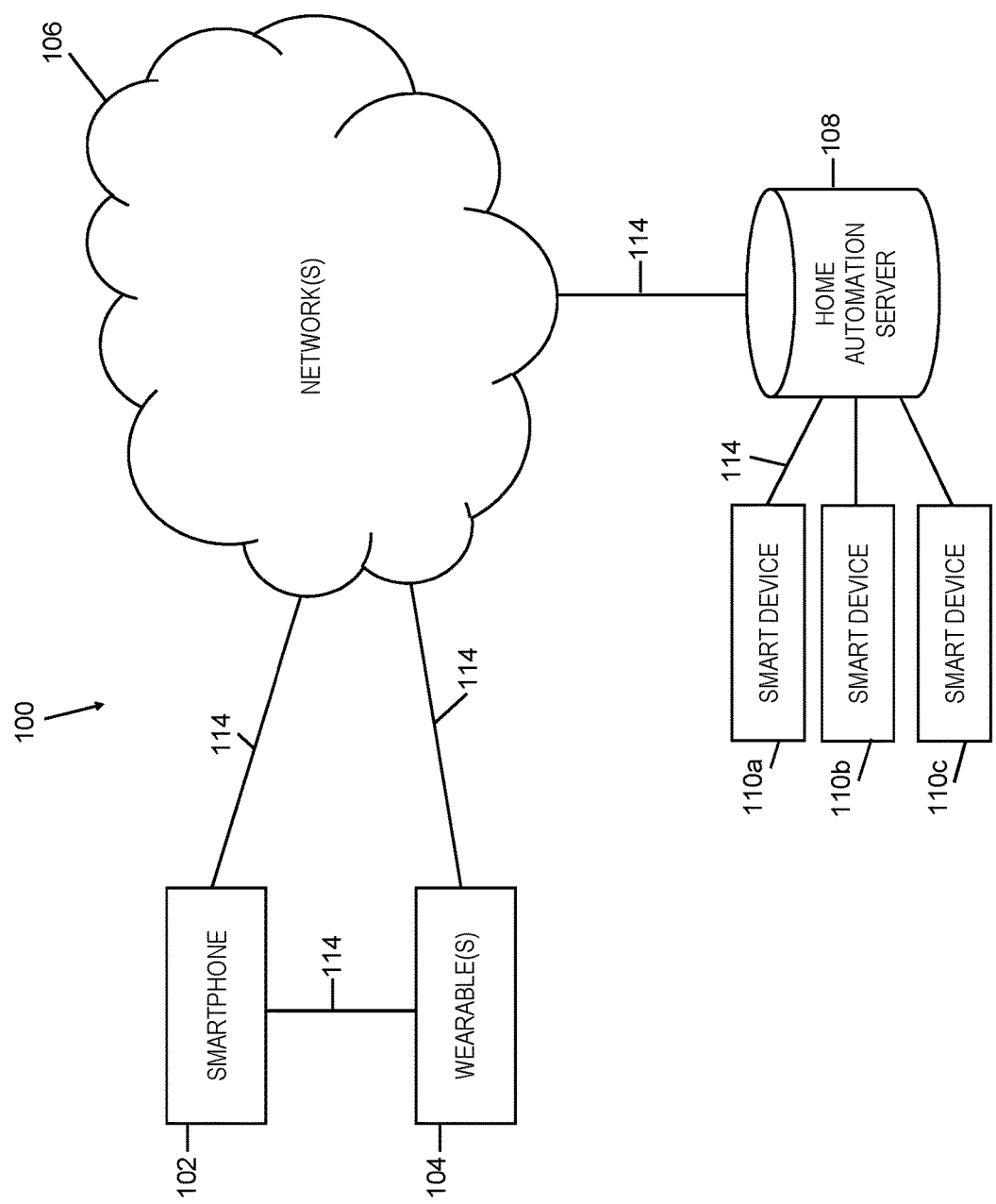
FIG. 1 depicts an example environment to incorporate and/or use aspects described herein.

FIG. 1 depicts an example environment to incorporate and/or use aspects described herein. Environment 100 includes a smartphone mobile device 102 of a user, the smartphone in communication with one or more wearable mobile devices ("wearables") 104 of the user. The communication is in one example a direct wireless connection, for instance a Bluetooth® wireless connection (BLUETOOTH is a registered trademark of Bluetooth SIG, Inc., Kirkland, Wash., U.S.A.). Smartphone 102 is in communication with network(s) 106, which may include any one or more networks, such as one or more local area networks and/or one or more wide area networks, such as the internet. In this example, wearable(s) 104 are also in communication directly with network(s) 106, though in other examples they may not have a separate connection to network(s) 106. Devices 102, 104 may be in communication with network(s) 106 via wired or wireless communications links, such as wired and/or cellular, Wi-Fi, or other types of wireless connections.

Also included in the environment are a plurality of devices (110a, 110b, 110c), which may be devices of environment 100 in which a user of smartphone 102 and wearable(s) 104 is present. Devices 110a, 110b, 110c are smart devices in this example, in communication with a home automation server 108 that is installed in the environment in which the user is present. Devices 110a, 110b, 110c are in communication with network(s) 106 via the home automation server 108, which in some examples takes commands from one or more other devices, such as smartphone 102 or remote, cloud-based controllers to control smart devices 110a, 110b, 110c. An example home automation server 108 is a smart hub device that connects wired or wirelessly to the user's home network, router or modem (not depicted) for internet access to communicate with the smart devices and external devices. In other examples, one or more of devices 110a, 110b, 110c connect directly to the internet in order communicate with external devices.

The components in FIG. 1 form wired or wireless network(s), and communication between the devices takes place via wired or wireless communications links 114 for communicating data between the devices. FIG. 1 is just one example of an environment to incorporate and use aspects described herein.

In some aspects, wearable device(s), a user's smartphone, tablet, or other mobile device, and a mobile device application installed on the mobile device are leveraged to predict onset of a particular health affliction and help address this onset. While examples provided herein involve wearable and other mobile devices, other types of computer systems may be utilized, for instance laptops, personal computers, and the like. Typically, wearables and other mobile devices incorporate sensors that can be leveraged as described herein, while laptops and desktop machines typically do not include these components, though there is no reason they could not if desired. However, in some aspects, processing described herein that utilizes, e.g., sensor or other measurement data in predicting whether a user will experience a particular health condition may run on such non-mobile devices like a user's desktop computer if desired, as may additional processing such as processing to interact with or control smart devices to perform functions such as dimming lights or adjusting sound volumes.

Methods provided herein can work on two levels: helping to predict the onset of a health affliction for a given time, and, once a health affliction attack happens, helping the user deal with it by entering a state or mode meant to help the user cope with the affliction. To forecast migraine attacks, for instance, a method can monitor a combination of variables, such as environmental conditions, stress levels, sleep alterations, and hormonal alterations, as examples, to acquire measurements of the plurality of conditions that a user is experiencing. To help the user deal with an active migraine, the method can configure device(s) of an environment in which the user is present to reduce effects of the device(s) on symptoms of the migraine by adjusting respective state(s) of each device of the device(s). For instance, it could adjust the smartphone's brightness, sound levels and notifications/alerts policy, among other options, in order to avoid conditions that would normally exacerbate the symptoms of a migraine. State of a device can refer to settings, operating parameters, characteristics, or the like, as examples.

Based on measurements of conditions that the user experiences, a prediction may be made as to whether the user will experience a migraine at that time or in the relatively near future. The prediction can be made using a logistic regression classifier based on a model obtained from training data(X,y), where X is a list of feature vectors and y a list of positive or negative migraine attack predictions, one for each vector in X. In a particular example, the process prompts the user for information including gender, date of birth, location, menstrual cycle dates (if user is female; menstruation is a statistically significant contributor to migraine episodes), and times of the day at which the user would like to receive a migraine prediction.

Then, the method attempts on a daily basis, in some examples, a prediction for each of the times of the day that the user has configured. For each prediction, the method could compute a feature vector by obtaining, e.g.:

Resting heart rate (leveraging, for example, an application programing interface (API) of a wearable device that incorporates a heart rate monitor). Heart rate may be an indicator of stress level. The method can obtain heart rate and/or heart rate variability to measure stress levels in the user, a factor that has a high correlation with migraines. This may be done via a specific heart rate monitoring device, such as a wearable, or alternatively via a technique that makes use of built-in features of the user's smartphone, such as the smartphone camera, to obtain the measurements.

Latest sleep score (using, for example, and API of a sleep tracker). If the system is configured to attempt more than one prediction per day, this data might be the same for multiple predictions of the same day, since the user may not have updated data for that variable if the user did not sleep between these predictions. Sleep alterations are frequently related to migraines. Processing described herein may itself monitor the user's sleep or, alternatively, may consume data from sleep tracking devices or applications. It may consume the APIs/services provided by these devices or applications and monitor the data obtained to look for alterations in sleep during extended periods.

Measurements of environmental conditions such as mean barometric pressure, temperature, humidity, and/or air quality (using, for example, a weather service's historical conditions and air quality APIs). This can monitor weather variables that are often related to migraine crises. Environmental measurement data can be data from sensors of wearable or other devices, or can be extrapolated from historic data (temperature, air quality, etc.), the latter of which may be especially applicable if sensors or the latest acquired data is/are not available at the time a prediction is to be made.

Hormonal alterations, such as whether the user is currently in a menstrual cycle (based on the information gathered at configuration time). In cases of adult premenopausal female users, the setup can ask question(s)

to generate a basic menstrual calendar for the user. This information can be used to track menstrual episodes when the user is most likely to have a migraine crises related to this hormonal alteration.

The data may be aggregated with the measurements from a configurable number N of previous prediction feature vectors. Each feature vector can encompass values from multiple readings/measurements—current measurements and one or more sets of prior measurements. This may be configurable; the user may be able to configure a parameter representing the window (how far back in history) the measurements on which a prediction is based should stretch. This is a control on how much history will be considered in predicting an upcoming migraine episode.

For example, for N=3, the feature vectors after day three could have the following form:

[restHeartRate {val0, val1, . . . , val3}, sleepScore {val0, val1, . . . , val3}, meanPressure {val0, val1, . . . , val3}, meanTemp {val0, val1, . . . , val3}, airQuality {val0, val1, . . . , val3}, inMenstrualCycle (0 or 1)], where the zero item (val0) represents a current measurement and items {val1, . . . , val3} represent the last three measurements for that condition. For male users and female users not currently menstruating, inMenstrualCycle would be False or 0.

Subsequently, a prediction could be attempted for the feature vector by means of a logistic regression classifier, examples of which include a Support Vector Machine (SVC), AdaBoost, or discriminant analysis approach. The classifier could use the model obtained from the current values in the (X,y) data set.

The user's smartphone or other mobile device can eventually obtain an indication of whether the prediction, positive or negative, was correct. If so, that prediction it associated with a 'Yes' or positive indication. If not, the prediction is associated with a No or negative indication. This will result in an accurate new feature vector with an actual positive or negative as to whether the prediction was correct. This new feature vector can be added to X and the new prediction to y. Then, the model may be retrained using this updated information.

Thus, a process can acquire the measurements of the conditions and add those to a measurement dataset that includes (i) the acquired measurements, as current measurements, of the conditions, and (ii) historical measurements of the conditions. The measurement dataset can include feature vectors, with each feature vector of the feature vectors (i) corresponding to a respective prior prediction made at a prior time about whether the user would experience the particular health affliction and (ii) corresponding to a respective positive or negative indication of whether the user experienced the particular health affliction. The feature vector can include measurements, of the historical measurements, of the conditions at the prior time and at one or more times before the prior time. In this manner, each feature vector has data that was current at the corresponding time, as well as additional reading(s) from before that prior time, and it is associated with an affirmative Yes or No indication of whether the health affliction occurred. Predicting, at a next time, whether the health affliction is likely to be experienced by the user can leverage a binary classifier based on a model built from the feature vectors to determine whether the user will experience the particular health affliction. Eventually, a new feature vector is added to the measurement dataset, the new feature vector including (i) the current measurements of the conditions and (ii) measurements, of the historical measurements, of the conditions at a configurable one or more times before a time at which the current measurements were acquired. The method can associate the new feature vector with a positive or negative indication of whether the user experienced the particular health affliction, and then retrain the model using at least some of the feature vectors and using the added new feature vector. The oldest feature vector(s) may be omitted, for instance, and not factor into the retraining, on the basis that they include too historic of information to be relevant.

In some embodiments, the (X,y) data set satisfies the following invariants:

X is a list of feature vectors, one for each prediction made;
For each vector X[i], there is a unique migraine prediction y[i] confirmed as being positive (confirmed correct) or negative (confirmed incorrect); and
Each vector X[i] includes the data from the measurements at the time of the prediction plus the measurements from the last min(N,i) feature vectors, corresponding to the last min(N,i) predictions (N being a configurable parameter).

In some examples, the regression and application of the model to current data to predict whether a migraine episode is to be expected is performed by the user's smartphone or other mobile device. Alternatively, the processing could instead be performed on a remote server, such as one offered by a cloud-based facility, or a combination of the two. In this regard, current smartphone technology is generally very capable of performing such a regression with minimal consumption of smartphone resources, though it may be desired to offload that processing for resource consumption or other reasons.

Figure 2:
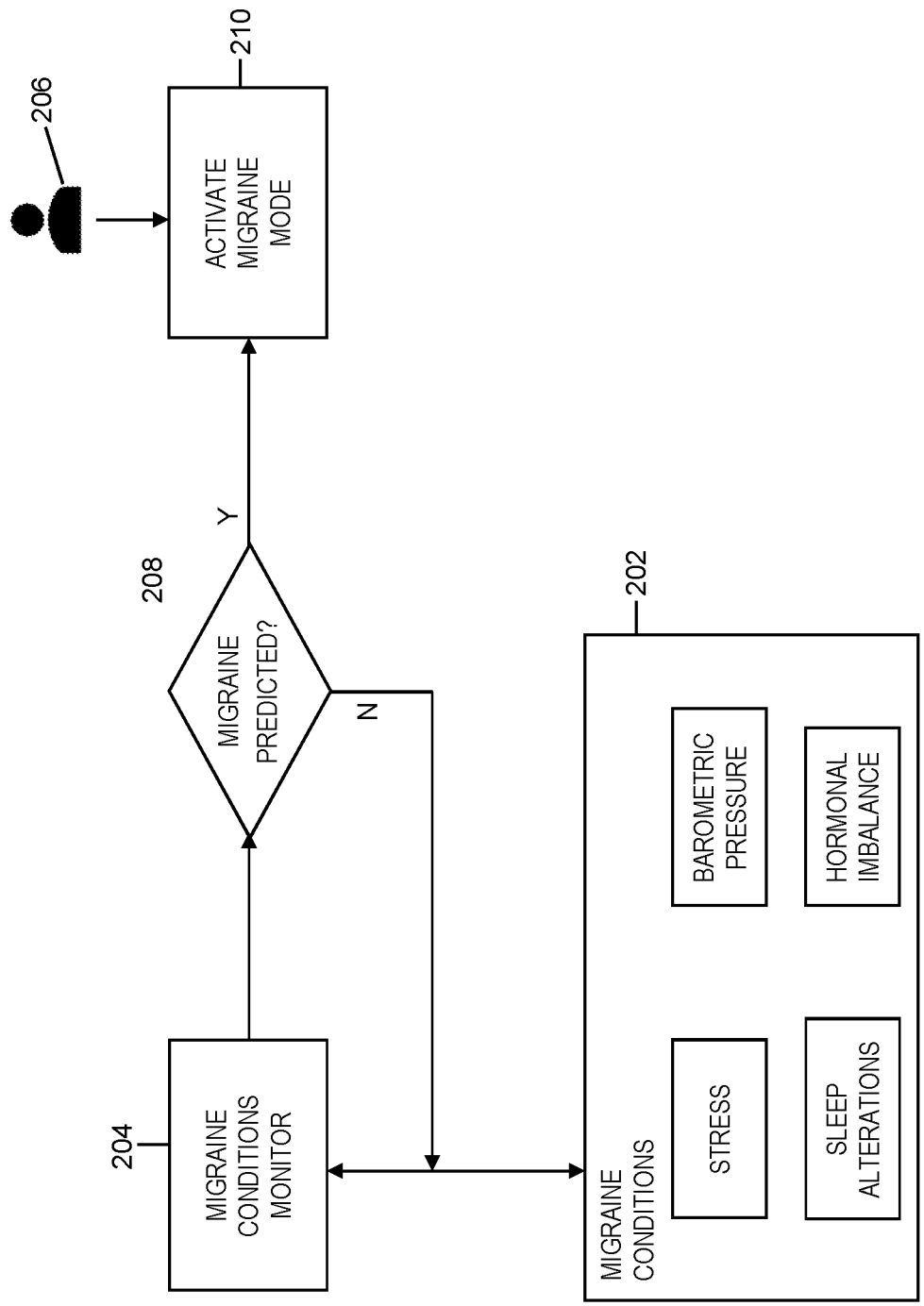
FIG. 2 depicts a conceptual diagram of prediction and device state configuration, in accordance with aspects described herein.

FIG. 2 depicts a conceptual diagram of prediction and device mode configuration for the particular case of migraine prediction, in accordance with aspects described herein. Migraine conditions 202 that are monitored by a migraine conditions monitor 204 include stress, barometric pressure, sleep alterations, and hormonal imbalances. The conditions monitor 204 may be implemented by software, for instance an app executing on a mobile device of the user 206. The monitoring activity can include acquiring measurements of the conditions, which are a combination of internal conditions internal to the user and external conditions external to the user. The monitoring occurs and a determination 208 is made as to whether a binary classifier classifies the measurements as positive or negative indicators of a migraine attack. For instance, a high-stressed female lacking sleep while menstruating and subject to a high barometric pressure condition may be likely to experience a migraine attack.

If the binary classifier does not make a positive prediction based on the measurements (208, N), the process returns and continues with the monitoring. Otherwise, if a migraine is predicted (208, Y), then a process activates a migraine mode 210. In this mode, as explained in further detail below, the process can automatically configure device(s) such as the user's smartphone, wearables, smart home devices, and any other devices, to reduce their effects on the migraine symptoms, for instance minimize the amount of light and sound they emit. In some examples, it places a device in a Do Not Disturb or similar setting that blocks or prevents various forms of alerts or distractions.

In other aspects, the user 206 can manually activate the migraine mode 210. This may be done in instances where the prediction was incorrect—the user was predicted not to experience a migraine at a given time but nevertheless experienced a migraine. Alternatively, perhaps the system was not configured to make a prediction for a given time when the user happened to experience the affliction, in which case the system would not have checked whether to place the device(s) in migraine mode.

In some examples, a user's manual activation signals the system that a migraine was experienced, and the system learns from that, for instance by correlating the attack to measurement data taken when the attack was indicated by the user. In examples where a prediction of no attack was made but the user manually activates the mode, the system can take that as an indication that the prediction was not correct, and log as updated data for retraining the prediction model.

As noted, the predicting may be performed on a schedule set by the user, for instance one or two times a day at specified times. The system can report each prediction result to the user, or alternatively report only when it predicts an attack to occur. Additionally or alternatively, predictions can be made on an ongoing basis that occur relatively frequently and automatically in the background, for instance every 10 minutes, every time the user moves to a different location, or upon any other desired trigger condition. However, the predictor may be configured to request input from the user to indicate each prediction as being correct or incorrect. In the case of repeated and frequent predictions, a prompt to the user with every prediction might be burdensome. Thus, in some applications, it may not be practical for the predictor to run with such frequency. In some cases, the automatic frequent predicting could take place for a limited period of time, such as an hour or two, under conditions when it would make sense for such aggressive monitoring. An example is during a workout or other high-stress activity that could trigger onset of the health affliction. Another example is when the smartphone or other mobile device performing the measurement data gathering and predicting senses that the user has on a wearable or other supporting device that can provide current measurement data for predictions. Consequently, the exact times when the predicting occurs need not be statically defined and may instead be dynamically and automatically determined.

A binary classifier to perform the predictions may be based on a model built from the feature vectors as described above. Aspects can adjust the model over time to result in more accurate predictions.

With respect to false positive predictions, if the user rejects the enabling of the migraine mode after an (incorrect) positive prediction, the prediction can be reverted to a negative indication: y[last_prediction_index]=False. With respect to false negative predictions, if the user sets/enables the migraine mode manually after an (incorrect) negative prediction, the prediction can be reverted to a positive indication: y[last_prediction_index]=True. In both cases, after correcting y, the method can retrain the logistic regression model from the updated (X,y) data set.

Initially, prior to collection of measurement data and establishing the feature vectors, there may not be sufficient data to produce the features vectors to build a model capable of accurate predictions. This could be addressed as one option by providing a cloud-based repository of samples for the (X,y) data set, the samples being from users authorizing upload of data set entries to the cloud. This upload could be made anonymous, in which only entries in the (X,y) data set along with location, age, and gender information are provided to the cloud, thus involving no personally identifiable information. The method could prompt a new user of aspects described herein whether he/she desires to start with an initial dataset randomly sampled from the cloud data (but selecting entries from users matching as closely as possible gender, age, and location of the new user). In this way, new users could benefit from crowd-sourced migraine predictions. The cloud repository could itself be seeded by recruiting a group of volunteers willing to use the application during a fixed period for the primary purpose of growing the repository rather than receiving meaningful predictions.

Once an initial dataset is collected about each user, say after 5 or 10 predictions, it may be desired to base subsequent predictions on only that user's data, though in other embodiments, it may be desired to utilize an aggregated dataset that aggregates the user's data with data of similar users. Whether to use only data of the user or a more expansive set of data may depend on the extent to which the user is an outlier in terms of the triggers of his/her health affliction. In yet another example, a weighted composite of data is used that weights the user's data more heavily than data of other users in the predicting.

After forecasting/predicting a possible migraine attack, or after the user states explicitly that he/she is having a migraine attack, an application running on a device (e.g. the user's smartphone, server, controller, etc.) can alert the user and offer different actions to take depending on the actual state of the user. If the application predicts a migraine episode for a specific time that the user requested, then the application could first prompt the user whether the user is experiencing the affliction, and then react if the user confirms that the user is experiencing the affliction. Thus, if a migraine is predicted, the system can inform the user and ask whether the user is experiencing symptoms (to confirm/deny the prediction) or whether an action should be taken. In some examples, a user's indication to perform an action such as dimming the lights in the case of a migraine health affliction could be regarded by the system as an implicit 'Yes' that the prediction is correct.

The user might set the system to automatically take configuration actions when the health affliction is predicted by the system to take place. The automatic actions may include, in the case of a migraine, automatically dimming lights and taking other actions through smart devices, and setting a sound profile of the user's smartphone, perhaps with notification to the user, and perhaps asking the user to accept or confirm the automatic actions.

The configuration actions to reduce effects of the symptoms can depend on the particular context, for instance where the user is located. In the case of a migraine health affliction, two particular examples are provided to help the user overcome the migraine attack while avoiding exacerbating the symptoms, though many other example applications exist. The user's smartphone/mobile device may act differently in terms of configuring devices in the user's environment depending on the actual location, which may be determined based on the device's GPS functions or other location methods, such as network-based (Cellular, Wi-Fi) location detection. Thus, as an example, if the user is at home or other place with smart devices available for control, the device could work together with any of these existing features in the smart environment to setup a "migraine friendly" environment to have the effect of reducing effects of devices within this environment on symptoms of the migraine. Examples include adjusting the lighting by closing curtains, dimming lights, or lowering the artificial light brightness, turning off devices that can bother the user during the migraine attack like audio and video producing/emitting devices, and switching communication devices such as a doorbell or telephone to silent, do not disturb, or not available states/modes.

As another example, for instance if the user is not at home or other location where device configuration is available to adequately address the situation, the smartphone can perform an 'environment scan' to help the user determine a better, preferred location for the user to stay in case the user suffers from the migraine attack forecasted. In this case, the device may perform the following, as examples:

(i) use the device's camera to detect whether the current lightning of the location is likely to negatively affect the user. A default threshold of 500 lux may be set based on scientific studies of light thresholds, though the particular threshold value could be adjusted by the user if desired;

(ii) Use the device's microphone to detect whether the background noise of the location is at or below some low level (e.g. less than 84 dB, again based on scientific studies suggesting this as a threshold). As before, the threshold value could be adjusted by the user if desired.

(iii) As part of the environment scan, if the user is wearing a smart watch and/or using a smartphone with a gyroscope, the system could measure current heart rate, whether the user is moving, and/or other internal conditions. If heart rate is high and the user is not in motion, stress levels are likely on the rise. The application could advise the user to move to a quieter, less stressful place.

If the current location is not recommended as a place for the user to remain, the device may prompt the user about whether the user has access to a vehicle or other mode of transport and/or whether the user is in a state to drive home or to another target location as the preferred environment. If the user is prepared to drive to the preferred environment, the smartphone could use its GPS functionality to determine and provide a route to the preferred location that reduces the user's exposure to exacerbating conditions of the particular health affliction, such as by avoiding traffic as much as possible.

In the event that the user needs assistance, the device could offer to help the user obtain a ride or other transport to the preferred environment, for instance by interacting with services like a ride-sharing application or livery service to procure a ride for the person to the preferred environment.

Figure 3:
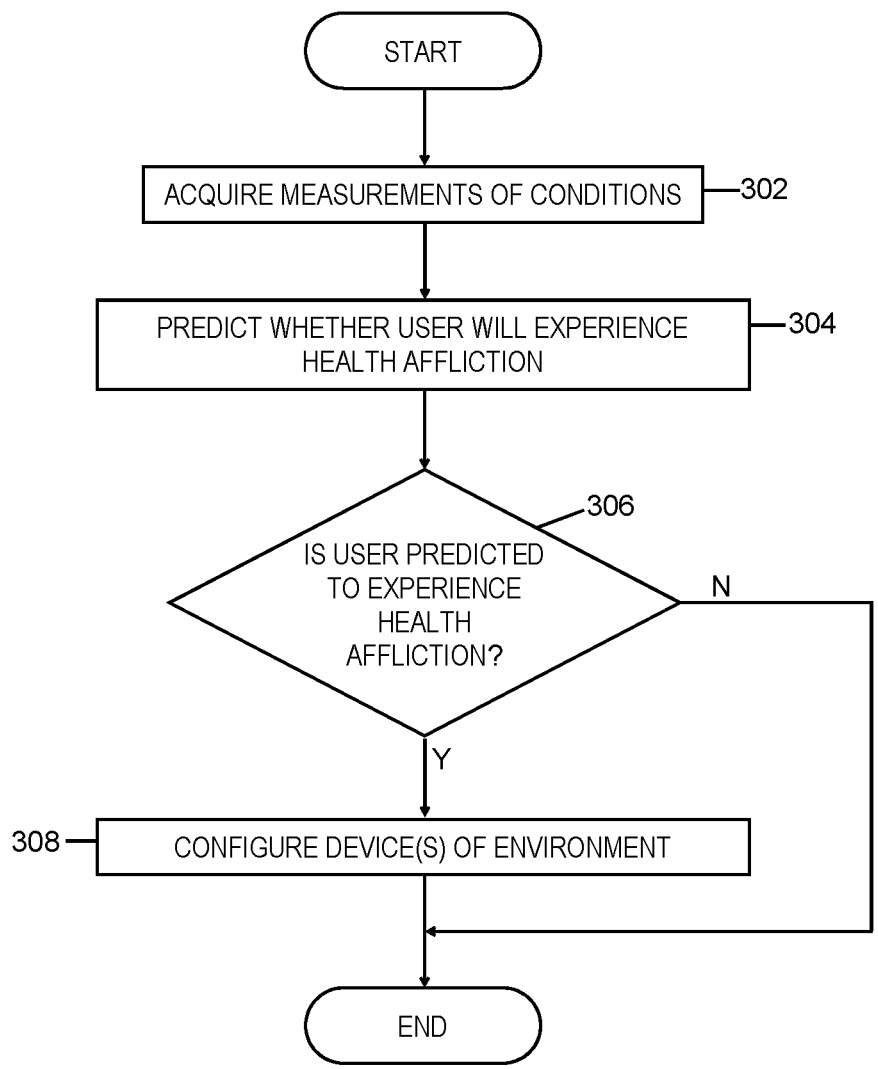
FIG. 3 depicts an example process for device configuration based on predicting a health affliction, in accordance with aspects described herein.

FIG. 3 depicts an example process for device configuration based on predicting a health affliction, in accordance with aspects described herein. Aspects of the process are performed by one or more computer systems, such as those described herein, which may include a mobile device of a user, such as a smartphone, a smart device, controller for a smart device, and/or one of more other computer systems.

The process begins by acquiring measurements of a plurality of conditions or variables that a user is experiencing (302). The plurality of conditions can include external conditions external to the user, such as at least one environmental condition of the environment in which the user is present. Example environmental conditions include ambient temperature, air quality, and level of light exposure. The plurality of conditions can additionally or alternatively include internal conditions internal to the user, such as stress level of the user, sleep properties of the user, hormonal properties of the user, and/or heart rate.

The process continues by predicting, based on the measurements, whether the user will experience a particular health affliction (304). In particular, the process can add the acquired measurements to a measurement dataset, the measurement dataset including the acquired measurements, as current measurements, of the plurality of conditions, and historical measurements of the plurality of conditions. The measurement dataset can include feature vectors, each feature vector of the feature vectors (i) corresponding to a respective prior prediction made at a prior time about whether the user would experience the particular health affliction and (i) corresponding to a respective positive or negative indication of whether the user experienced the particular health affliction. Additionally, each such feature vector can include measurements, of the historical measurements, of the plurality of conditions at the prior time (to which the feature vector corresponds) and at one or more times before that prior time. In this manner, each feature vector has data that was current at the prior time to which the feature vector corresponds as well as data of additional reading(s) from before that prior time, and the feature vector is associated with an affirmative positive or negative indication about whether the health affliction occurred for that prior time.

The predicting can leverage a binary classifier, based on a model built from these feature vectors, to determine whether the user will experience the particular health affliction.

The process of FIG. 3 continues by determining whether the user is predicted to experience the health affliction (306). Based on predicting that the user will experience the particular health affliction (306, Y), the process configures one or more devices of an environment in which the user is present to reduce effects of the one or more devices on symptoms of the particular health affliction (308). The configuring can include adjusting a respective at least one state of each device of the one or more devices. The state of a device may refer to settings, operating parameters, characteristics, or the like of the device.

In a particular embodiment, the environment includes a home of the user, and the configuring interacts with smart devices in the home of the user over a home network to which the smart devices are connected to alter the respective at least one state of each device of the devices. For instance, the configuring may include lowering curtains/blinds, dimming lights, and silencing the doorbell, as examples.

Additionally or alternatively, a device of the one or more devices that is configured can include a mobile device of the user, such as a smartphone, tablet, wearable, or other mobile device. The configuring the one or more devices can include enabling a policy of the mobile device to reduce effects of the mobile device on symptoms of the particular health affliction, the policy including a display brightness policy, a sound level policy, and/or a notification policy, as examples.

In some embodiments, the particular health affliction includes a migraine attack, and the configuring the one or more devices configures the one or more devices to reduce levels of light and sound emitted by the one or more devices, including levels of light and sound emitted from a mobile device of the user, for instance by way of adjusting display brightness and sound policies of the mobile device.

In some examples, acquiring the measurements includes collecting at least some measurements of the acquired measurements from a wearable device of the user by a mobile device of the user, and the mobile device performs the predicting and the configuring.

After configuring the device(s), or if instead at 306 it is determined that the user is not predicted to experience the health affliction at the given time, the process ends. In some embodiments, the user provides a prompted or unprompted positive or negative indication about whether the user is experiencing the health affliction, which may be used to confirm or refute the prediction. This can be indicated in a feature vector associated with the given time and prediction, and used in retraining a model for the predicting.

Figure 4:
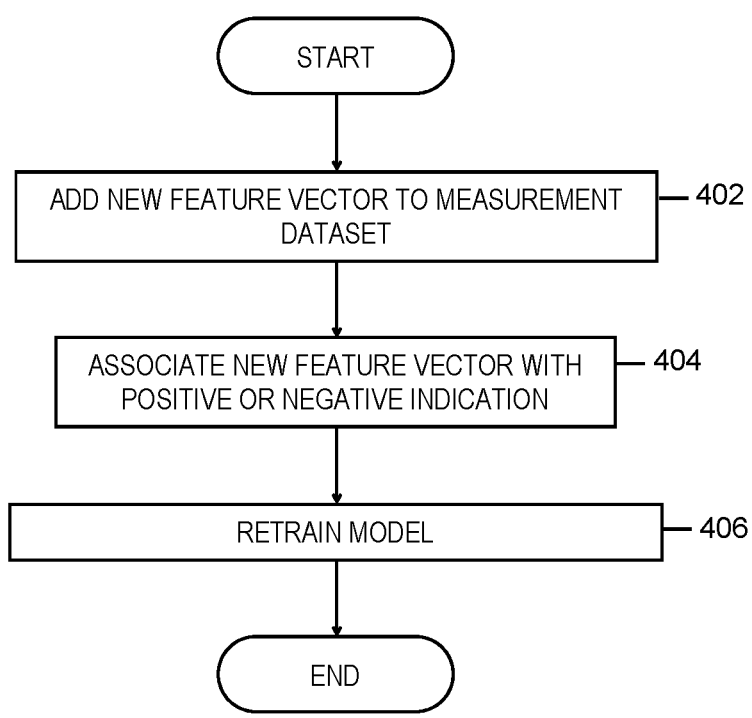
FIG. 4 depicts an example process for model retraining in accordance with aspects described herein.

FIG. 4 depicts an example process for model retraining in accordance with aspects described herein. Aspects of the process are performed by one or more computer systems, such as those described herein, which may include a mobile device of a user, such as a smartphone, a cloud-based server, and/or one of more other computer systems.

The process adds a new feature vector to the measurement dataset (402), the new feature vector including the current measurements of the plurality of conditions (current for the given time for which a prediction is made) and measurements, of the historical measurements, of the plurality of conditions at a configurable one or more times before a time at which the current measurements were acquired. In this manner, the new feature vector has the current (i.e. present time) measurements and one or more prior readings. The process then associates the new feature vector with a positive or negative indication of whether the prediction was correct or whether the user experienced the particular health affliction (404). A confirmed positive (Yes) or negative (No) as to whether the health affliction was experienced may be included with the new feature vector in order to complete that update of the training data for the model. The model is then retrained (406) using the newly added vector and additional other feature vectors included in the dataset, and the process ends. Since each feature vector corresponds to a different prior time, a setting regarding how historic the data on which to base future predictions should be may be configurable. A user's data about onset of the health affliction from a year ago for instance may no longer be useful at predicting more recent episodes of the health affliction.

If the health affliction is predicted to be experienced by the user, any of various actions may be taken. In some examples, a process obtains sensor data from one or more sensors of a mobile device of the user, and determines based on the sensor data whether the user should move from a current environment to a preferred environment. The current environment may present conditions that exacerbate symptoms of the affliction. Based on determining that the user should move to the preferred environment, the process could determine and provide, to the user, a route to the preferred environment that reduces exposure to exacerbating conditions of the particular health affliction. In a particular example, if the user is predicted to experience a migraine headache momentarily and the system determines that the user is in a bright, loud, outdoor environment, it may determine that the user should relocate to a quieter darker venue, such as the user's home or work. The system can then automatically generate a vehicle route to that preferred environment that minimizes exposure to traffic congestion and other exacerbating factors for migraine symptoms. Thus, the system could account for dynamic real time data, for instance traffic data, to determine the best route to take to the preferred environment. The configuring the device(s) may be performed based on the user moving to the preferred environment, where the preferred environment is the environment that has the one or more devices configured by the configuring. Thus, the system might navigate the user back home and automatically adjust the user's curtains, lights, and sound-producing devices prior to, or at the time of, the user's arrival to prepare that environment.

A user can separately manually indicate that the user is experiencing the particular health affliction, whether or not a prediction was made for that time and/or incorrectly predicted whether the affliction would occur. A process could repeat the configuring, wherein the repeating the configuring configures at least one device of some environment, in which the user is present at the another time, to reduce effects of the at least one device on symptoms of the particular health affliction, where repeating the configuring includes adjusting a respective at least one state of each device of the at least one device.

Although various examples are provided, variations are possible without departing from a spirit of the claimed aspects.

Figure 5:
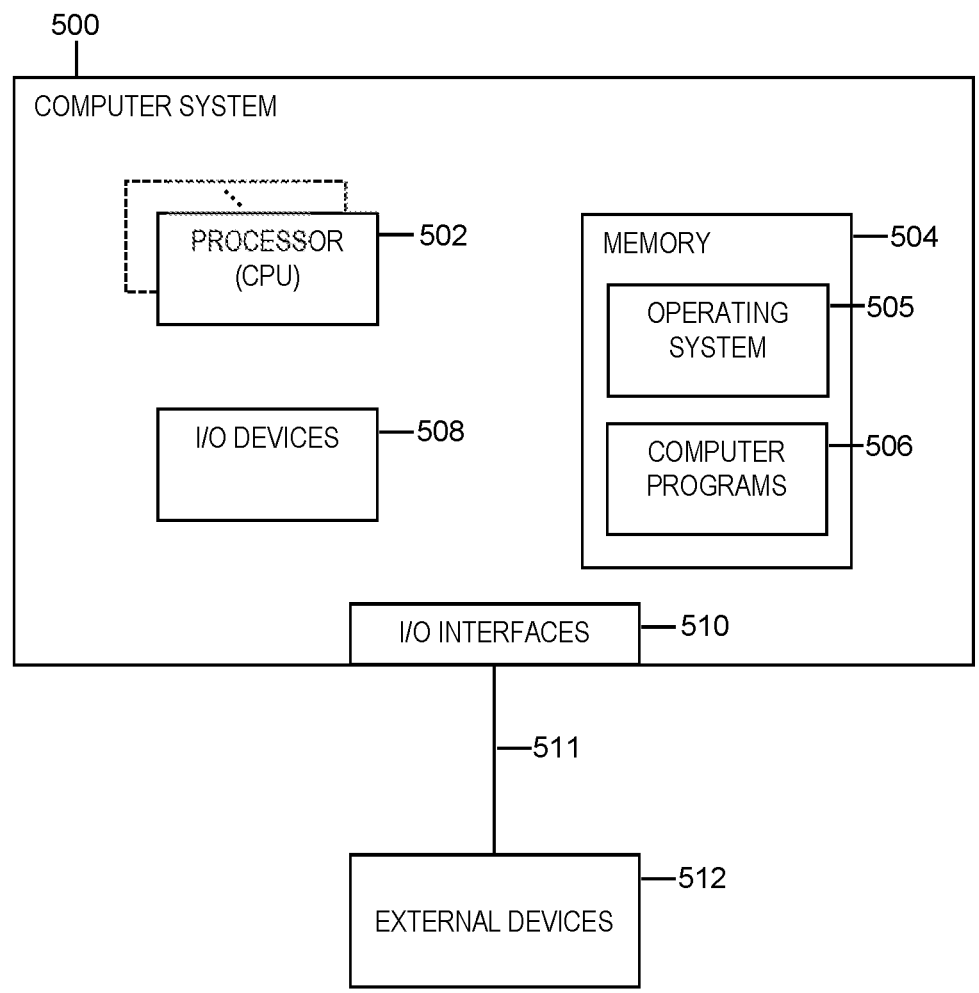
FIG. 5 depicts one example of a computer system and associated devices to incorporate and/or use aspects described herein.

Processes described herein may be performed singly or collectively by one or more computer systems, such as one or more mobile devices, cloud-based devices, servers, smart devices, automation controllers, or a combination of the foregoing, as examples. FIG. 5 depicts one example of such a computer system and associated devices to incorporate and/or use aspects described herein. A computer system may also be referred to herein as a data processing device/system, computing device/system/node, or simply a computer. The computer system may be based on one or more of various system architectures and/or instruction set architectures, such as those offered by International Business Machines Corporation (Armonk, N.Y., USA), Intel Corporation (Santa Clara, Calif., USA) or ARM Holdings plc (Cambridge, England, United Kingdom), as examples.

FIG. 5 shows a computer system 500 in communication with external device(s) 512. Computer system 500 includes one or more processor(s) 502, for instance central processing unit(s) (CPUs). A processor can include functional components used in the execution of instructions, such as functional components to fetch program instructions from locations such as cache or main memory, decode program instructions, and execute program instructions, access memory for instruction execution, and write results of the executed instructions. A processor 502 can also include register(s) to be used by one or more of the functional components. Computer system 500 also includes memory 504, input/output (I/O) devices 508, and I/O interfaces 510, which may be coupled to processor(s) 502 and each other via one or more buses and/or other connections. Bus connections represent one or more of any of several types of bus structures, including a memory bus or memory controller, a peripheral bus, an accelerated graphics port, and a processor or local bus using any of a variety of bus architectures. By way of example, and not limitation, such architectures include the Industry Standard Architecture (ISA), the Micro Channel Architecture (MCA), the Enhanced ISA (EISA), the Video Electronics Standards Association (VESA) local bus, and the Peripheral Component Interconnect (PCI).

Memory 504 can be or include main or system memory (e.g. Random Access Memory) used in the execution of program instructions, storage device(s) such as hard drive(s), flash media, or optical media as examples, and/or cache memory, as examples. Memory 504 can include, for instance, a cache, such as a shared cache, which may be coupled to local caches (examples include L1 cache, L2 cache, etc.) of processor(s) 502. Additionally, memory 504 may be or include at least one computer program product having a set (e.g., at least one) of program modules, instructions, code or the like that is/are configured to carry out functions of embodiments described herein when executed by one or more processors.

Memory 504 can store an operating system 505 and other computer programs 506, such as one or more computer programs/applications that execute to perform aspects described herein. Specifically programs/applications can include computer readable program instructions that may be configured to carry out functions of embodiments of aspects described herein.

Examples of I/O devices 508 include but are not limited to microphones, speakers, Global Positioning System (GPS) devices, cameras, lights, accelerometers, gyroscopes, magnetometers, sensor devices configured to sense light, proximity, heart rate, body and/or ambient temperature, blood pressure, and/or skin resistance, and activity monitors. An I/O device may be incorporated into the computer system as shown, though in some embodiments an I/O device may be regarded as an external device (512) coupled to the computer system through one or more I/O interfaces 510.

Computer system 500 may communicate with one or more external devices 512 via one or more I/O interfaces 510. Example external devices include a keyboard, a pointing device, a display, and/or any other devices that enable a user to interact with computer system 500. Other example external devices include any device that enables computer system 500 to communicate with one or more other computing systems or peripheral devices such as a printer. A network interface/adapter is an example I/O interface that enables computer system 500 to communicate with one or more networks, such as a local area network (LAN), a general wide area network (WAN), and/or a public network (e.g., the Internet), providing communication with other computing devices or systems, storage devices, or the like. Ethernet-based (such as Wi-Fi) interfaces and Bluetooth® adapters are just examples of the currently available types of network adapters used in computer systems.

The communication between I/O interfaces 510 and external devices 512 can occur across wired and/or wireless communications link(s) 511, such as Ethernet-based wired or wireless connections. Example wireless connections include cellular, Wi-Fi, Bluetooth®, proximity-based, near-field, or other types of wireless connections. More generally, communications link(s) 511 may be any appropriate wireless and/or wired communication link(s) for communicating data.

Particular external device(s) 512 may include one or more data storage devices, which may store one or more programs, one or more computer readable program instructions, and/or data, etc. Computer system 500 may include and/or be coupled to and in communication with (e.g. as an external device of the computer system) removable/non-removable, volatile/non-volatile computer system storage media. For example, it may include and/or be coupled to a non-removable, non-volatile magnetic media (typically called a "hard drive"), a magnetic disk drive for reading from and writing to a removable, non-volatile magnetic disk (e.g., a "floppy disk"), and/or an optical disk drive for reading from or writing to a removable, non-volatile optical disk, such as a CD-ROM, DVD-ROM or other optical media.

Computer system 500 may be operational with numerous other general purpose or special purpose computing system environments or configurations. Computer system 500 may take any of various forms, well-known examples of which include, but are not limited to, personal computer (PC) system(s), server computer system(s), such as messaging server(s), thin client(s), thick client(s), workstation(s), laptop(s), handheld device(s), mobile device(s)/computer(s) such as smartphone(s), tablet(s), and wearable device(s), multiprocessor system(s), microprocessor-based system(s), telephony device(s), network appliance(s) (such as edge appliance(s)), virtualization device(s), storage controller(s), set top box(es), programmable consumer electronic(s), network PC(s), minicomputer system(s), mainframe computer system(s), and distributed cloud computing environment(s) that include any of the above systems or devices, and the like.

Aspects described herein may be incorporated into and/or use a cloud computing environment. It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for loadbalancing between clouds).

A cloud computing environment is service oriented with a focus on statelessness, low coupling, modularity, and semantic interoperability. At the heart of cloud computing is an infrastructure comprising a network of interconnected nodes. One such node is node 10 depicted in FIG. 6.

Computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

Figure 6:
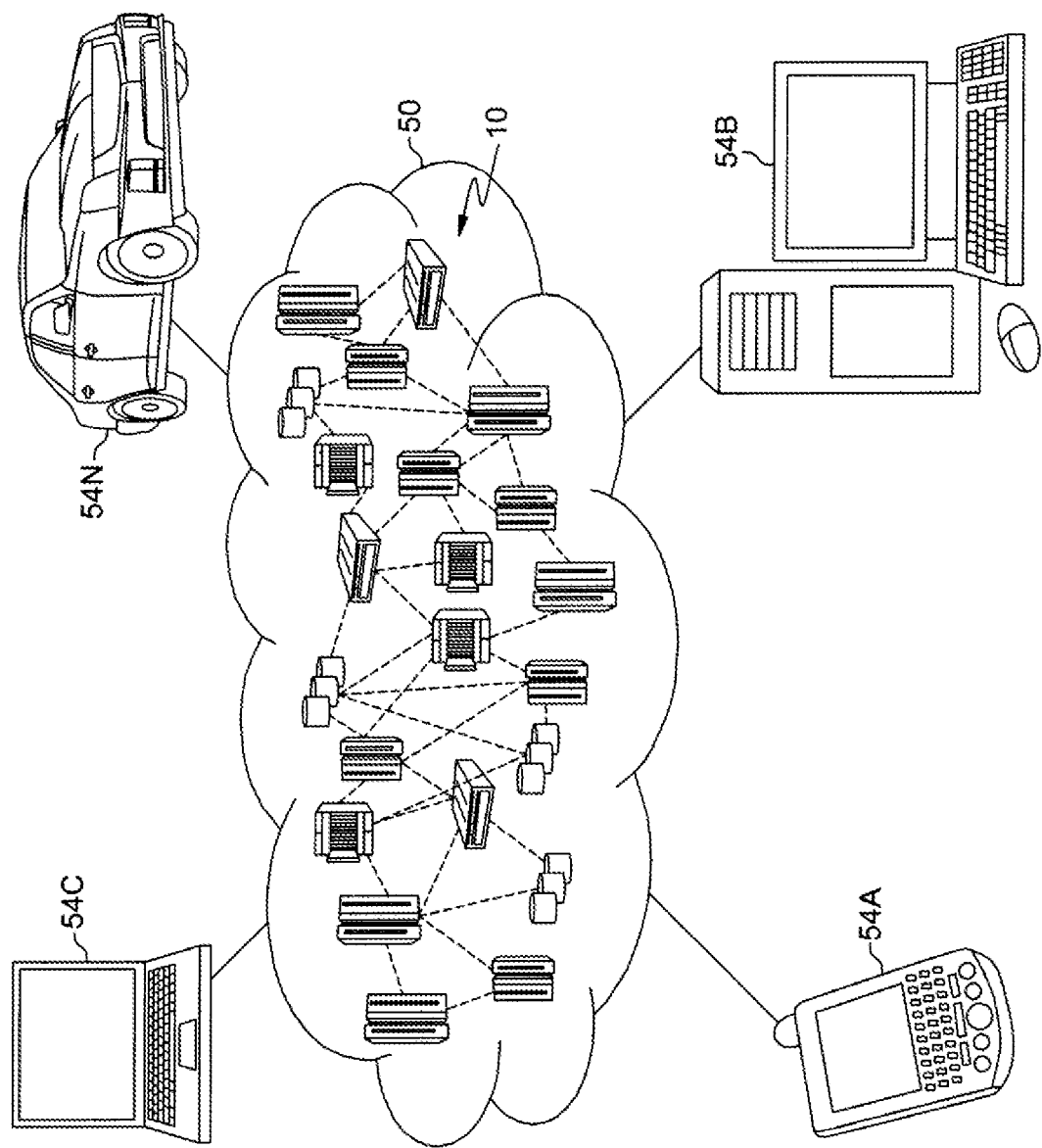
FIG. 6 depicts a cloud computing environment according to an embodiment of the present invention.

Referring now to FIG. 6, illustrative cloud computing environment 50 is depicted. As shown, cloud computing environment 50 comprises one or more computing nodes 10 with which local computing devices used by cloud consumers, such as, for example, smartphone or other mobile device 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
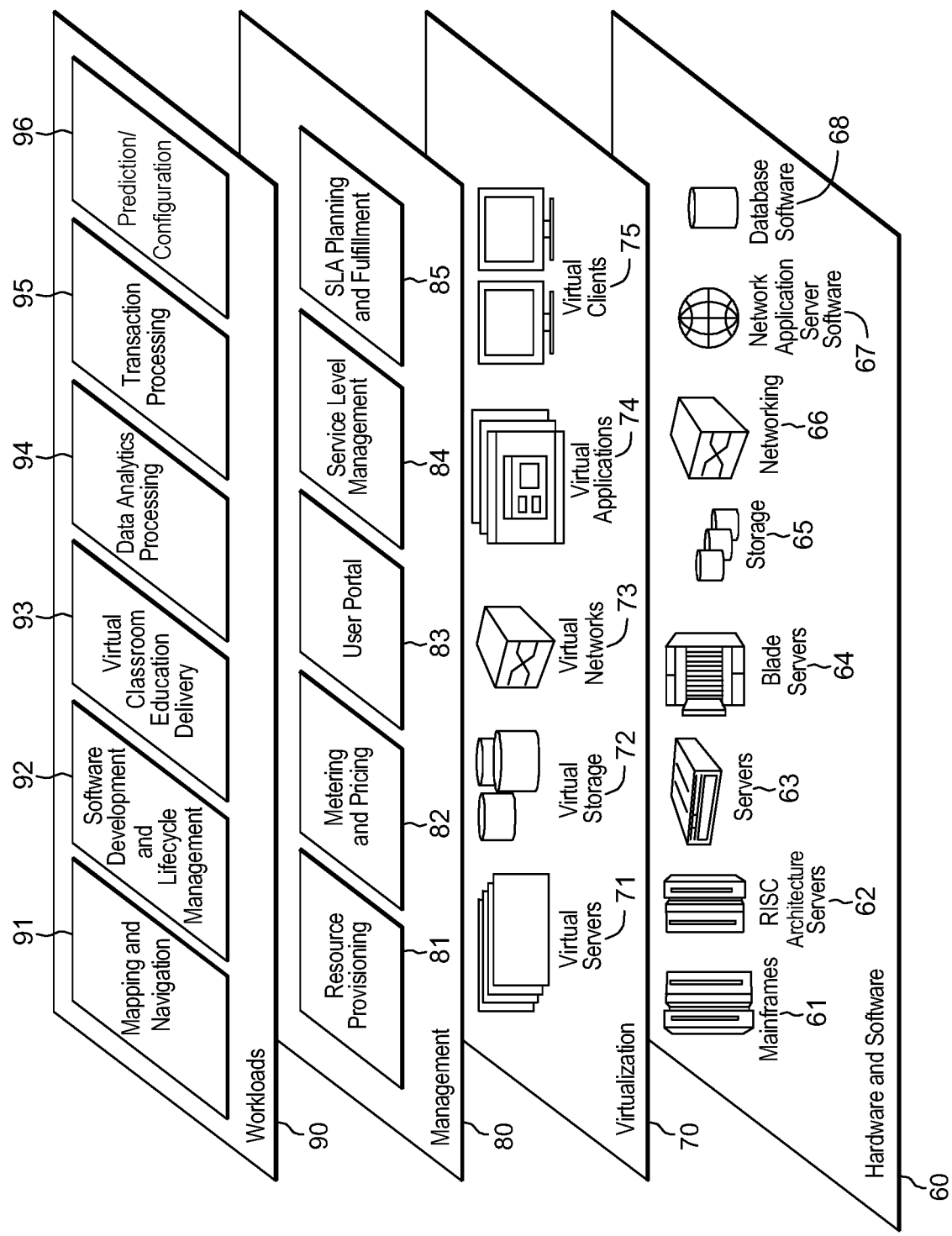
FIG. 7 depicts abstraction model layers according to an embodiment of the present invention.

Referring now to FIG. 7, a set of functional abstraction layers provided by cloud computing environment 50 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and health affliction prediction and device configuration 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In addition to the above, one or more aspects may be provided, offered, deployed, managed, serviced, etc. by a service provider who offers management of customer environments. For instance, the service provider can create, maintain, support, etc. computer code and/or a computer infrastructure that performs one or more aspects for one or more customers. In return, the service provider may receive payment from the customer under a subscription and/or fee agreement, as examples. Additionally or alternatively, the service provider may receive payment from the sale of advertising content to one or more third parties.

In one aspect, an application may be deployed for performing one or more embodiments. As one example, the deploying of an application comprises providing computer infrastructure operable to perform one or more embodiments.

As a further aspect, a computing infrastructure may be deployed comprising integrating computer readable code into a computing system, in which the code in combination with the computing system is capable of performing one or more embodiments.

As yet a further aspect, a process for integrating computing infrastructure comprising integrating computer readable code into a computer system may be provided. The computer system comprises a computer readable medium, in which the computer medium comprises one or more embodiments. The code in combination with the computer system is capable of performing one or more embodiments.

Although various embodiments are described above, these are only examples. For example, computing environments of other architectures can be used to incorporate and use one or more embodiments.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or step plus function elements in the claims below, if any, are intended to include any structure, material, or act for performing the function in combination with other claimed elements as specifically claimed. The description of one or more embodiments has been presented for purposes of illustration and description, but is not intended to be exhaustive or limited to in the form disclosed. Many modifications and variations will be apparent to those of ordinary skill in the art. The embodiment was chosen and described in order to best explain various aspects and the practical application, and to enable others of ordinary skill in the art to understand various embodiments with various modifications as are suited to the particular use contemplated.

What is claimed is:

1. A computer-implemented method comprising:
   acquiring measurements of a plurality of conditions that a user is experiencing;
   predicting, based on the measurements, whether the user will experience a particular health affliction, wherein the particular health affliction comprises a migraine attack, wherein a measurement dataset having historical measurements of the plurality of conditions includes feature vectors, each feature vector of the feature vectors corresponding to a respective prior prediction made at a prior time about whether the user would experience the particular health affliction and corresponding to a respective positive or negative indication of whether the user experienced the particular health affliction, and the feature vector comprising measurements, of the historical measurements, of the plurality of conditions at the prior time and at one or more times before the prior time, wherein the user controls how much historical data is to be considered in making predictions of whether the user will experience the particular health affliction by configuring a parameter for the feature vectors, the parameter representing a size of a window of measurements on which predictions are to be based, and wherein the predicting whether the user will experience the particular health affliction uses a model built from the feature vectors subject to the configured parameter to determine whether the user will experience the particular health affliction; and
   based on predicting that the user will experience the particular health affliction, the particular health affliction having symptoms exacerbated by operation of one or more devices of an environment in which the user is present, configuring the one or more devices to reduce effects of the one or more devices on the symptoms of the particular health affliction, the configuring comprising adjusting a respective at least one state of each device of the one or more devices, wherein a device of the one or more devices comprises a mobile device of the user, and wherein the configuring the one or more devices comprises enabling a policy of the mobile device to reduce effects of the mobile device on symptoms of the migraine attack by adjusting production and emission of signals by and from the mobile device, the policy comprising a display brightness policy that controls brightness of a display screen of the mobile device and a sound level policy, wherein enabling the policy configures the mobile device to reduce levels of light and sound emitted from the mobile device of the user, the light being emitted from the display screen of the mobile device.

2. The method of claim 1, wherein the plurality of conditions comprise external conditions external to the user, the external conditions comprising at least one environmental condition of the environment in which the user is present.

3. The method of claim 1, wherein the plurality of conditions comprise internal conditions internal to the user, the internal conditions comprising at least one selected from the group consisting of: stress level of the user, sleep properties of the user, a hormonal property of the user, and heart rate.

4. The method of claim 1, wherein the environment comprises a home of the user, wherein the configuring interacts with smart devices in the home of the user over a home network to which the smart devices are connected to alter the respective at least one state of each device of the one or more devices.

5. The method of claim 1, wherein the acquiring comprises collecting at least some measurements of the acquired measurements from a wearable device of the user by the mobile device of the user, wherein the mobile device performs the predicting and the configuring.

6. The method of claim 1, further comprising adding the acquired measurements to the measurement dataset, the measurement dataset comprising the acquired measurements, as current measurements, of the plurality of conditions, wherein the predicting leverages a binary classifier, based on the model built from the feature vectors, to determine whether the user will experience the particular health affliction.

7. The method of claim 6, further comprising:
   adding a new feature vector to the measurement dataset, the new feature vector comprising the current measurements of the plurality of conditions and measurements, of the historical measurements, of the plurality of conditions at a configurable one or more times before a time at which the current measurements were acquired;
   associating the new feature vector with a positive or negative indication of whether the user experienced the particular health affliction; and
   retraining the model, the retraining using at least some of the feature vectors and using the added new feature vector.

8. The method of claim 1, further comprising:
   obtaining sensor data from one or more sensors of the mobile device of the user;
   determining based on the sensor data whether the user should move from a current environment to a preferred environment; and
   based on determining that the user should move to the preferred environment, determining and providing, to the user, a route to the preferred environment that reduces exposure to exacerbating conditions of the particular health affliction, wherein the configuring is performed based on the user moving to the preferred environment and the preferred environment is the environment having the one or more devices configured by the configuring.

9. The method of claim 1, further comprising, based on the user indicating, at another time, that the user is experiencing the particular health affliction, repeating the configuring, wherein the repeating the configuring configures at least one device of another environment, in which the user is present at the another time, to reduce effects of the at least one device on symptoms of the particular health affliction, the repeating the configuring comprising adjusting a respective at least one state of each device of the at least one device.

10. A computer program product comprising:
a computer readable storage medium readable by a processor and storing instructions for execution by the processor for performing a method comprising:
acquiring measurements of a plurality of conditions that a user is experiencing;
predicting, based on the measurements, whether the user will experience a particular health affliction, wherein the particular health affliction comprises a migraine attack, wherein a measurement dataset having historical measurements of the plurality of conditions includes feature vectors, each feature vector of the feature vectors corresponding to a respective prior prediction made at a prior time about whether the user would experience the particular health affliction and corresponding to a respective positive or negative indication of whether the user experienced the particular health affliction, and the feature vector comprising measurements, of the historical measurements, of the plurality of conditions at the prior time and at one or more times before the prior time, wherein the user controls how much historical data is to be considered in making predictions of whether the user will experience the particular health affliction by configuring a parameter for the feature vectors, the parameter representing a size of a window of measurements on which predictions are to be based, and wherein the predicting whether the user will experience the particular health affliction uses a model built from the feature vectors subject to the configured parameter to determine whether the user will experience the particular health affliction; and
based on predicting that the user will experience the particular health affliction, the particular health affliction having symptoms exacerbated by operation of one or more devices of an environment in which the user is present, configuring the one or more devices to reduce effects of the one or more devices on the symptoms of the particular health affliction, the configuring comprising adjusting a respective at least one state of each device of the one or more devices, wherein a device of the one or more devices comprises a mobile device of the user, and wherein the configuring the one or more devices comprises enabling a policy of the mobile device to reduce effects of the mobile device on symptoms of the migraine attack by adjusting production and emission of signals by and from the mobile device, the policy comprising a display brightness policy that controls brightness of a display screen of the mobile device and a sound level policy, wherein enabling the policy configures the mobile device to reduce levels of light and sound emitted from the mobile device of the user, the light being emitted from the display screen of the mobile device.

11. The computer program product of claim 10, wherein the environment comprises a home of the user, wherein the configuring interacts with smart devices in the home of the user over a home network to which the smart devices are connected to alter the respective at least one state of each device of the one or more devices.

12. The computer program product of claim 10, wherein the method further comprises:
adding the acquired measurements to the measurement dataset, the measurement dataset comprising the acquired measurements, as current measurements, of the plurality of conditions, wherein the predicting leverages a binary classifier, based on the model built from the feature vectors, to determine whether the user will experience the particular health affliction;
adding a new feature vector to the measurement dataset, the new feature vector comprising the current measurements of the plurality of conditions and measurements, of the historical measurements, of the plurality of conditions at a configurable one or more times before a time at which the current measurements were acquired;
associating the new feature vector with a positive or negative indication of whether the user experienced the particular health affliction; and
retraining the model, the retraining using at least some of the feature vectors and using the added new feature vector.

13. The computer program product of claim 10, wherein the method further comprises:
obtaining sensor data from one or more sensors of the mobile device of the user;
determining based on the sensor data whether the user should move from a current environment to a preferred environment; and
based on determining that the user should move to the preferred environment, determining and providing, to the user, a route to the preferred environment that reduces exposure to exacerbating conditions of the particular health affliction, wherein the configuring is performed based on the user moving to the preferred environment and the preferred environment is the environment having the one or more devices configured by the configuring.

14. A computer system comprising:
a memory; and
a processor in communication with the memory, wherein the computer system is configured to perform a method comprising:
acquiring measurements of a plurality of conditions that a user is experiencing;
predicting, based on the measurements, whether the user will experience a particular health affliction, wherein the particular health affliction comprises a migraine attack, wherein a measurement dataset having historical measurements of the plurality of conditions includes feature vectors, each feature vector of the feature vectors corresponding to a respective prior prediction made at a prior time about whether the user would experience the particular health affliction and corresponding to a respective positive or negative indication of whether the user experienced the particular health affliction, and the feature vector comprising measurements, of the historical measurements, of the plurality of conditions at the prior time and at one or more times before the prior time, wherein the user controls how much historical data is to be considered in making predictions of whether the user will experience the particular health affliction by configuring a parameter for the feature vectors, the parameter representing a size of a window of measurements on which predictions are to be based, and wherein the predicting whether the user will experience the particular health affliction uses a model built from the feature vectors subject to the configured parameter to determine whether the user will experience the particular health affliction; and based on predicting that the user will experience the particular health affliction, configuring one or more devices of an environment in which the user is present to reduce effects of the one or more devices on symptoms of the particular health affliction, the configuring comprising adjusting a respective at least one state of each device of the one or more devices, wherein a device of the one or more devices comprises a mobile device of the user, and wherein the configuring the one or more devices comprises enabling a policy of the mobile device to reduce effects of the mobile device on symptoms of the migraine attack by adjusting production and emission of signals by and from the mobile device, the policy comprising a display brightness policy that controls brightness of a display screen of the mobile device and a sound level policy, wherein enabling the policy configures the mobile device to reduce levels of light and sound emitted from the mobile device of the user, the light being emitted from the display screen of the mobile device.

15. The computer system of claim 14, wherein the environment comprises a home of the user, wherein the configuring interacts with smart devices in the home of the user over a home network to which the smart devices are connected to alter the respective at least one state of each device of the one or more devices.

16. The computer system of claim 14, wherein the method further comprises:
- obtaining sensor data from one or more sensors of the mobile device of the user;
- determining based on the sensor data whether the user should move from a current environment to a preferred environment; and
- based on determining that the user should move to the preferred environment, determining and providing, to the user, a route to the preferred environment that reduces exposure to exacerbating conditions of the particular health affliction, wherein the configuring is performed based on the user moving to the preferred environment and the preferred environment is the environment having the one or more devices configured by the configuring.

* * * * *